US008983663B2

(12) United States Patent
Marar

(10) Patent No.: US 8,983,663 B2
(45) Date of Patent: Mar. 17, 2015

(54) SELF-GUIDED PORTABLE MEDICAL DIAGNOSTIC SYSTEM

(75) Inventor: Rajeev Ramankutty Marar, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 2124 days.

(21) Appl. No.: 11/550,156

(22) Filed: Oct. 17, 2006

(65) Prior Publication Data

US 2008/0161672 A1 Jul. 3, 2008

(51) Int. Cl.
| A61B 5/05 | (2006.01) |
| B25J 9/00 | (2006.01) |
| A61B 5/055 | (2006.01) |
| A61B 6/00 | (2006.01) |
| A61B 5/00 | (2006.01) |
| A61B 8/00 | (2006.01) |

(52) U.S. Cl.
CPC .............. *A61B 8/4405* (2013.01); *A61B 5/055* (2013.01); *A61B 6/4405* (2013.01); *A61B 8/00* (2013.01); *A61B 2560/0431* (2013.01); *Y10S 901/01* (2013.01)
USPC ................ 700/264; 700/258; 700/246; 901/1

(58) Field of Classification Search
CPC ........................... A61B 6/4401; A61B 6/4405
USPC ....................... 700/246, 258–259, 264; 901/1
See application file for complete search history.

(56) References Cited

U.S. PATENT DOCUMENTS

| 5,600,305 | A | | 2/1997 | Stafford et al. |
| 5,867,561 | A | * | 2/1999 | Strasser et al. ............... 378/98.2 |
| 6,262,659 | B1 | * | 7/2001 | Korkosz et al. .......... 340/539.24 |
| 6,494,831 | B1 | * | 12/2002 | Koritzinsky .................. 600/301 |
| 6,497,661 | B1 | | 12/2002 | Brock-Fisher |
| 6,782,285 | B2 | * | 8/2004 | Birkenbach et al. .......... 600/407 |
| 6,817,866 | B1 | * | 11/2004 | Ginzburg et al. ............. 434/365 |
| 7,066,291 | B2 | * | 6/2006 | Martins et al. ................ 180/167 |
| 2003/0160877 | A1 | | 8/2003 | Sumida |
| 2003/0219100 | A1 | * | 11/2003 | Okoda ......................... 378/102 |
| 2004/0093252 | A1 | * | 5/2004 | Maekawa .......................... 705/8 |
| 2004/0093650 | A1 | * | 5/2004 | Martins et al. ..................... 901/1 |
| 2005/0033124 | A1 | | 2/2005 | Kelly |
| 2005/0131740 | A1 | * | 6/2005 | Massenzio et al. ............... 705/2 |
| 2005/0216126 | A1 | * | 9/2005 | Koselka et al. ............... 700/259 |
| 2007/0061041 | A1 | * | 3/2007 | Zweig ........................... 700/245 |
| 2007/0192910 | A1 | * | 8/2007 | Vu et al. .......................... 901/17 |
| 2007/0198128 | A1 | * | 8/2007 | Ziegler et al. ................. 700/245 |
| 2007/0199108 | A1 | * | 8/2007 | Angle et al. ..................... 901/17 |
| 2007/0238949 | A1 | * | 10/2007 | Wang et al. ................... 600/407 |
| 2008/0013692 | A1 | * | 1/2008 | Maschke ....................... 378/198 |
| 2008/0081992 | A1 | * | 4/2008 | Kagermeier .................. 600/425 |
| 2009/0125147 | A1 | * | 5/2009 | Wang et al. ................... 700/264 |
| 2009/0177323 | A1 | * | 7/2009 | Ziegler et al. ................. 700/259 |
| 2011/0274244 | A1 | * | 11/2011 | Jabri et al. ....................... 378/62 |

* cited by examiner

*Primary Examiner* — Khoi Tran
*Assistant Examiner* — Dale Moyer
(74) *Attorney, Agent, or Firm* — Fletcher Yoder, P.C.

(57) ABSTRACT

The present invention provides a medical diagnostic device with an automatic moving mechanism. The device comprises an input interface for receiving instructions from an operator or from a remote device. A motion controller is coupled to the input interface for controlling movements of the diagnostic device based on the instructions received through the input interface. A moving assembly is coupled to the motion controller for moving the diagnostic device under control of the motion controller. In an embodiment, a method of guiding a portable imaging system through various locations in a hospital is disclosed. Also the invention discloses a self-guided portable imaging system.

22 Claims, 6 Drawing Sheets

SELF-GUIDED PORTABLE MEDICAL DIAGNOSTIC SYSTEM

FIELD OF THE INVENTION

This invention generally relates to a medical diagnostic system and more particularly to a portable medical diagnostic system with an automatic moving mechanism.

BACKGROUND OF THE INVENTION

In the current diagnostic and medical imaging technology, many portable diagnostic or imaging devices are used. However the portable medical imaging or diagnostic devices today rely on the operator pushing the device within the hospital, sometimes with the help of power assisted devices. The operator has to move the device from its parking place to various patient locations using manual force. This could include typically moving the equipment across different floor locations as well as different areas of the hospital. There involves many problems in manually operating the portable device. One of the significant problems is wastage of manpower in operating the devices. Also it requires a lot of manual effort in physically moving the portable devices all around the hospital. Today many hospitals use portable imaging devices very often to cover huge areas of the hospital, moving from one corner of the site to another. This will become cumbersome if there is a need for retake especially in the case of equipment failure.

Another problem existing in the field is in deciding an optimal route for the movement of the device. The operator may follow a regular route assigned to him or else he may decide a route, which he may consider desirable. The operator needs to consider many parameters in deciding the optimal route. This may include, number of patients to be scanned, their location, emergency situations, hospital layout, room allocation, number of floors, availability of concerned doctor, etc. So many times the operator will not be able to decide an optimal route manually. This will lead to wastage of time and inefficient use of the device. This problem will became more significant in the case of bigger hospitals where there are different floors and increased numbers of patients to be scanned. In this event the optimal route to be selected carefully to avoid wastage of time.

Thus there exists a need to design medical imaging or diagnostic devices which are easier to move within hospitals. There also exists a need to provide a system that makes it easier to determine an optimal route for the imaging or diagnostic device.

SUMMARY OF THE INVENTION

The above-mentioned shortcomings, disadvantages and problems are addressed herein which will be understood by reading and understanding the following specification.

One embodiment of the present invention provides a medical diagnostic device with an automatic moving mechanism including: an input interface for receiving instructions; a motion controller coupled to the input interface for controlling movements of the medical diagnostic device based on the instructions received through the input interface; and a moving assembly coupled to the motion controller for moving the medical diagnostic device under control of the motion controller. In different embodiments, the medical diagnostic device is configured to be a medical imaging device or a patient monitoring device.

In another embodiment, a method of guiding a portable imaging system to locations in a hospital is provided. The method includes the steps of: preparing a route map based on hospital data, the hospital data including hospital information; obtaining a work list, the work list including patient information and job information; determining a navigation route for movement of the imaging system based on the work list and the route map; and moving the imaging system based on the navigation route. In different embodiments, the navigation route is prepared by having a user manually enter the navigation route or is prepared automatically by the imaging system.

In yet another embodiment, a self-guided portable medical imaging system is provided. The system includes: a medical imaging device; a robotic controller coupled to the medical imaging device, the robotic controller including: a processor configured to guide the movement of the medical imaging device using a work list and a route map; and a moving assembly operably coupled to the processor for moving the medical imaging device.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

In various embodiments, an imaging system with an automatic moving mechanism is described. A portable imaging or diagnostic device with an automatic moving mechanism for moving the device without any manual effort of an operator is disclosed. In an embodiment, the automatic moving mechanism associated with the imaging device is configured to accept commands from an external device for generating a navigation route for the movement of the imaging or diagnostic device.

While the present technique is described herein with reference to medical imaging applications, it should be noted that the invention is not limited to this or any particular application or environment. Rather, the technique may be employed in a range of medical diagnostic devices including medical imaging devices and patient monitoring devices including electrocardiographic (ECG) monitoring devices, blood pressure monitoring devices, anaesthesia monitoring devices, and other medical devices that are typically moved within a hospital environment. It is noted that such devices may be used in hospitals, healthcare clinics, nursing homes, and other healthcare facilities that will be collectively referred to herein as "hospitals". The present invention may also be used outside healthcare environments in non-medical imaging and diagnostic devices such as devices used for baggage screening, quality control, and so forth, to mention but a few.

In an embodiment, the invention provides a method of guiding a portable imaging system to various locations in a hospital. The method involves the step of generating a navigation route for the movement of the device. As mentioned earlier, even though the technique is explained with reference to a hospital environment, the application of the method is not restricted to the same.

In another embodiment, the invention describes a self-guided portable medical imaging system. The embodiment suggests a fully automated imaging device, which does not require an operator for moving the imaging device.

Figure 1:
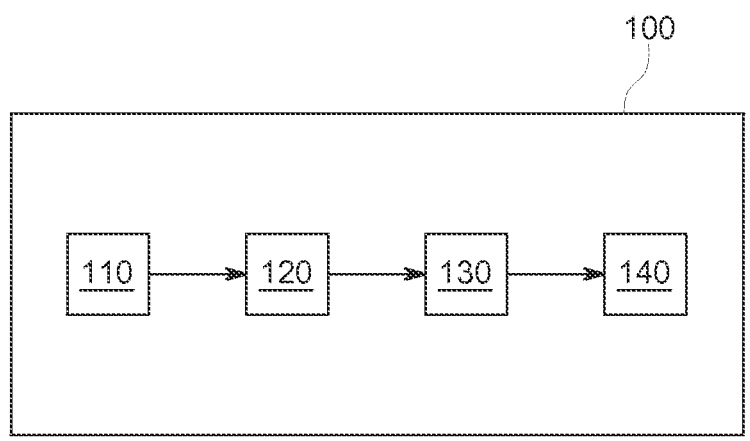
FIG. 1 is a block diagram of an imaging system with an automatic moving mechanism as described in an embodiment of the invention.

FIG. 1 illustrates diagrammatically an imaging system with an automatic moving mechanism as described in an embodiment of the invention. The imaging system 100 is provided with an imaging device 120. The medical imaging device 120 may be selected from any medical imaging devices such as computed tomography device, a positron emission tomography device, a magnetic resonance imaging device, an ultrasound imaging device and an X-ray device, but need not be limited to these. In an embodiment the imaging device 120 is provided with an input interface and the input interface is a user interface 100. The user interface 110 acts as an interface between the imaging device 120 and a user or an operator. The user or operator may be located within the hospital premises or at a remote location. The user interface 110 may be provided as an integral part of the imaging device 120 or may be associated with the imaging device separately. The user interface 110 may be wireless or a wired interface. The user or operator provides the instructions to the imaging device 120 through the user interface 110. In different embodiments the user interface 110 may be a wired interface such as a key board, joystick, camera, speakers, microphones or antennas and a wireless interface such as a transceiver for transmitting and receiving signals from a remote device. A motion controller 130 is provided with the imaging device 120 to control the movements of the imaging device 120. The user interface 110 is coupled with the motion controller 130. While FIG. 1 illustrates an embodiment wherein the user interface 110 is coupled to the motion controller 130 indirectly through the imaging device 120, the user interface 110 may also be coupled directly to the motion controller 130 in other embodiments. The motion controller 130 receives the instructions from the user or operator through the user interface 110.

In an embodiment the motion controller 130 generates signals based on the instructions received through the user interface 10. The motion controller 130 may include a processor configured to generate signals based on the instructions received from the user. The motion controller 130 furnishes both power and control signals for movement of the imaging device 120, including deciding an optimal route for the movement of the imaging device 120. The motion controller 130 may also execute various signal processing functions for the various inputs received from different user interfaces such as joystick, keyboard, camera, speaker etc. In general, the motion controller 130 commands navigation of the imaging system 100 to execute the imaging. The motion controller 130 may also include signal processing circuitry, typically based upon a general purpose or application-specific digital computer, associated memory circuitry for storing programs and routines executed by the computer, as well as configuration parameters and image data, interface circuits, and so forth.

The motion controller 130 is further coupled to a moving assembly 140. The moving assembly 140 is capable of moving the imaging device laterally, vertically and rotationally. The moving assembly 140 is capable of supporting the multidirectional movements of the imaging device 120. In an embodiment the moving assembly 140 is configured to allow a linear and a 360 degree rotational movement of the imaging device 120. In an embodiment the moving assembly 140 includes a set of wheels or tracks capable of moving the imaging device 120 in various directions. The moving assembly is configured to receive signals from the motion controller for moving the medical diagnostic device automatically without real-time manual control by a user.

In an embodiment the moving assembly is configured to receive instructions or signals from the motion controller 130 and to move the imaging device 120 in accordance with the instructions or signals. Alternately the imaging device 120 may be moved by manually pushing the imaging device.

Figure 2:
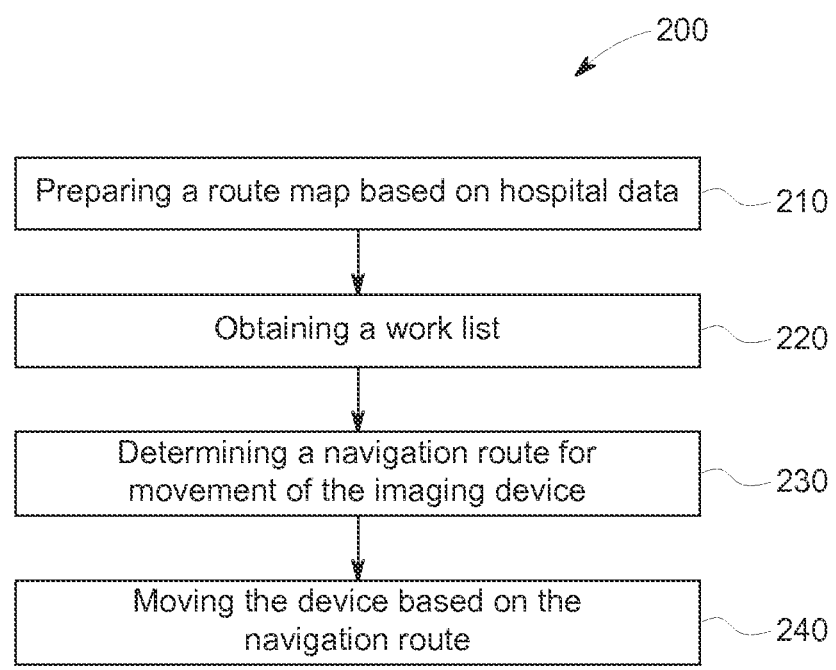
FIG. 2 is a high level flowchart depicting exemplary steps of a method of guiding a portable imaging system to various locations in a hospital as described in an embodiment of the invention.

FIG. 2 is a high level flowchart depicting exemplary steps of a method of guiding a portable imaging system to various locations in a hospital as described in an embodiment of the invention. The method of guiding 200 is explained in context of a hospital using a medical imaging device. At step 210, a route map is prepared based on hospital data. The hospital data includes hospital information like hospital layout, the number of patients to be scanned, their location, emergency situations, room allocation, number of floors, elevators, availability of concerned doctor etc, but need not be limited to this. The hospital information may be provided to the imaging system by an operator or the hospital information may be fetched by the imaging system from a server. Based on the hospital information a route map is prepared. In an embodiment the operator may provide the route map to the imaging system through a user interface. Alternately, a route map may be defined by the imaging system with the help of the hospital information. For calculating the route map various reference locations are used. For example, the imaging system is provided with different reference points like position of elevator, the scanning rooms in each floor etc. Based on this information the imaging system will be able to derive a route map of the hospital. Alternately the imaging system may fetch the route map from a server. At step 220, a work list is obtained. The work list includes the patient information and job information. The patient information may include the details of the patient for example name, address, age, sex, past medical records etc. The job information may include details like schedule of scanning, body part to be scanned, suitable imaging device needs to be used for scanning, concerned doctor, any other priority details, etc. In an embodiment the work list is fed by an operator to the imaging system manually. Alternately the work list is fetched from a server by the imaging system. At step 230, a navigation route is determined for the movement of the imaging device. The navigation route includes defining the movement paths of the imaging device based on the work list and the route map. The movement paths may be defined automatically or manually. Based on the route map and the work list, the imaging system will generate automatically a navigation route for the imaging device. Alternately a navigation route may be provided to the imaging system by an operator. Also a server may define the navigation route and the imaging system may fetch the navigation route from the server. At step 240, the imaging device is moved based on the navigation route. This may be achieved by either manually pushing the imaging device based on the navigation route defined or by providing an automatic moving mechanism in association with the imaging system. The automatic moving mechanism should be capable of receiving instructions from the imaging system or from a user and based on the instructions, the moving mechanism should move the imaging system automatically without any manual intervention.

Figure 3:
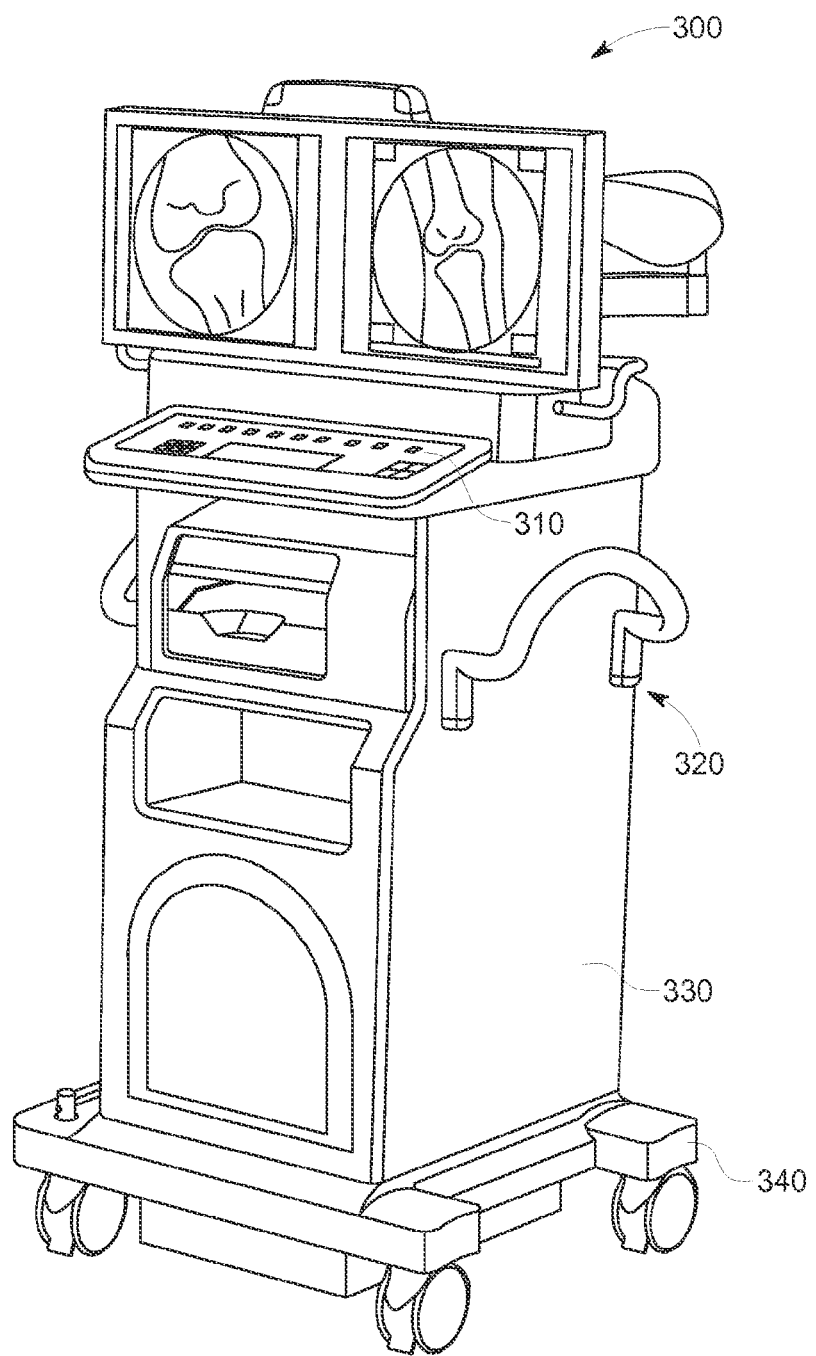
FIG. 3 illustrates an exemplary imaging device with an automatic moving mechanism.

FIG. 3 illustrates an exemplary imaging device with an automatic moving mechanism. The imaging system 300 is provided with an imaging device 320. The imaging device 320 may be any medical imaging device such as a computed tomography device, a positron emission tomography device, a magnetic resonance imaging device, an ultrasound imaging device and an X-ray device, but need not be limited to these. The imaging device 320 is coupled with a user interface 310. The user interface 310 may be provided as an integral part of the imaging device or may be associated separately to the imaging device. The user interface 310 may use a wireless or a wired interface. The user interface 310 acts as a medium to interact the imaging device 320 with the user. The user provides instructions to the imaging device 320 through the user interface 310. The figure illustrates a keyboard as the user interface. The user interface 310 may be a wired interface such as keyboard, joy stick etc or a wireless interface such as a transceiver for transmitting and receiving signal to a remote operator.

In an embodiment the user interface 310 may include wireless as well as wired user interface. The wireless interface, such as a transceiver may be provided as an integral part of the user interface. Alternately a transceiver may be provided with the imaging device for transmitting and receiving signals. If the operator of the imaging device 320 is located in a remote location, the operator may operate the imaging device 320 through a wireless user interface. The instructions are received by the imaging device 320 through the transceiver. In an embodiment the transceiver may also include a coder for coding the instructions received to appropriate signals. In one embodiment, the same user interface is used for allowing an operator to control both the imaging functionality of the imaging device 320 and the movement of the imaging device 320. Alternatively, the user interface may include a first user interface portion for allowing an operator to control the imaging functionality of the imaging device 320 and a second user interface portion for allowing an operator (or another operator) to control the movement of the device 320.

The imaging system 300 also includes a motion controller 330 operably coupled to the user interface 310. The motion controller 320 receives the instructions from the user interface 310 and accordingly generates signals, which can control the movements of the imaging device 320. The motion controller 330 will fetch the details of the hospital including hospital layout plans, number of floors, scanning rooms, reference points, elevator details etc from a server (not shown). The server is provided in the hospital which may be any network server and may have a database storing hospital data including hospital layout plans, number of floors, scanning rooms, reference points, elevator details etc. Alternately an operator may enter this information to the imaging system through the user interface 310. Based on the hospital information, the motion controller 330 generates a route map. Alternately the operator may input a route map to the imaging system. Also the server may have a route map based on the hospital information and the imaging system may directly fetch the route map from the server. The motion controller 330 also fetches a work list from the server. The server may have a work list indicting patient information and job information. The patient information includes name, address, medical history, age, sex, details of diagnostics to be done, etc. The job information includes scanning schedule, desired imaging device, availability of the doctor, priority details, etc. Again based on the route map and the work list the motion controller 330 will generate a navigation map. Alternately the operator may provide a navigation route to the imaging system 300.

In an embodiment the motion controller 330 may be provided with a memory (not shown). The hospital data, worklist, route map or navigation route etc may be stored in the memory. During operation, the motion controller 330 may access the memory and may generate signals for controlling the movement of the imaging device 320.

The motion controller 330 is coupled to a moving assembly 340. The moving assembly 340 supports the movements of the imaging device 320. The moving assembly 340 includes a moving mechanism to move the device in multi-direction. The moving assembly 340 is configured to receive signals from the motion controller 330 and move the imaging device 320 in accordance with the signals. In an embodiment the moving assembly 340 includes a set of wheels, which are capable to drive the imaging device 320 in various directions. The assembly 340 includes tracks in another embodiment.

In an embodiment the imaging system 300 may be provided with a display (not shown), which may display the navigation route. An operator may manually push the imaging device 320 in accordance with the displayed navigation route. Alternately an automatic moving mechanism associated with the imaging device 320 may receive the navigation route or signals generated based on the navigation route from the motion controller 330 and move the imaging device accordingly.

Figure 4:
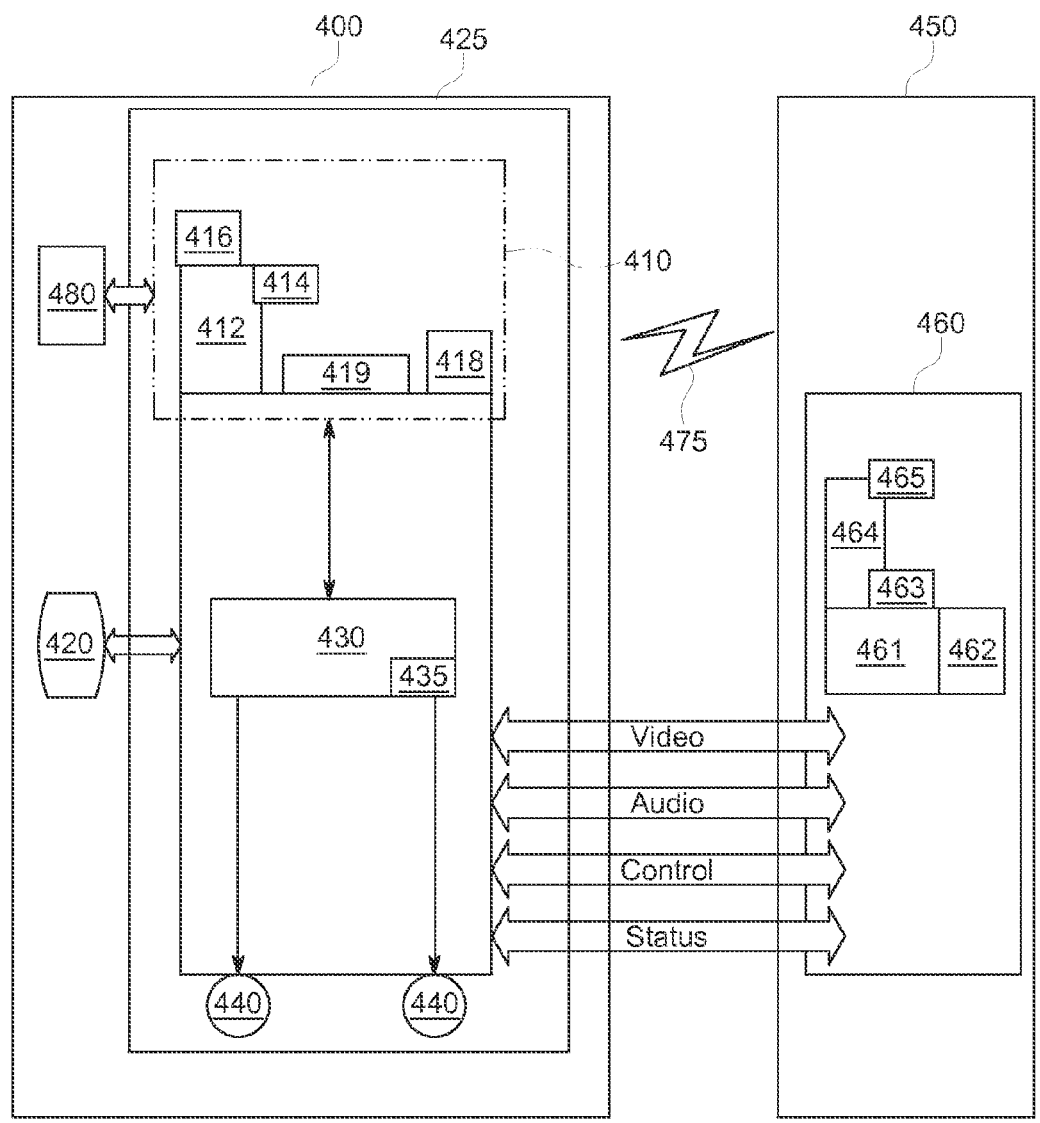
FIG. 4 illustrates a self-guided imaging device as described in an embodiment of the invention.

FIG. 4 illustrates a self-guided imaging device as described in an embodiment of the invention. In an embodiment guiding of the imaging device is explained in context of a hospital environment 400. The operator or user may be located in an operator environment 450, which may be located in a remote location. The hospital environment 400 includes an imaging device 420 and robotic controller 425, coupled to the imaging device 420. The imaging device 420 is a medical imaging device selected from a computed tomography device, a positron emission tomography device, a magnetic resonance imaging device, an ultrasound imaging device and an X-ray device, but need not be limited to these. The robotic controller 425 is configured to facilitate the automatic movement of the imaging device 420. The robotic controller 425 may or may not be an integral part of the imaging device. In an embodiment the robotic controller 425 is provided as a separate unit coupled to the imaging device 420. The robotic controller 425 comprises a user interface 410, a processor 430 and a moving assembly 440. The user interface 410 interacts with the operator environment 450 for carrying out the automatic movement of the imaging device 420. The user interface 410 may be wireless or wired interface and may communicate with the user or a remote device through a wired or wireless protocol. The user interface 410 may include different interfaces such as speaker 412, microphone 414, camera 416, antenna 418 and a display 419. The speaker 412 and the microphone 414 may be used to establish an aural communication between the operator and the imaging device 420.

The operator environment 450 may include a computer 460 that has a monitor 461, a camera 462, a microphone 463 and a speaker 464. The computer 460 may also have an input device 465 such as a joystick or a mouse. The operator environment 450 is typically located in a place that is remote from the hospital environment 400. Each operator environment computer 460 may operate Microsoft OS software and WINDOWS XP or other operating systems such as LINUX. The computer 460 may also operate a video driver, a camera driver, an audio driver and a joystick driver. The video images may be transmitted and received with compression software such as MPEG CODEC.

The camera 416 of the robot controller may be wirelessly coupled to the camera 462 of the operator environment. The operator transmits and receives the aural communication through the speaker 464 and the microphone 463.

In an embodiment the hospital environment 400 and the operator environment 450 interact through a network interface 475. The network interface 475 may be either a packet switched network such as the Internet, or a circuit switched network such has a Public Switched Telephone Network (PSTN) or other broadband system.

A server 480 also may be provided in the hospital environment 400. The server 480 may be any network server with a database having hospital information, work list etc. The hospital data may have hospital layout plans, number of floors, scanning rooms, reference points, elevator details etc. The work list may include patient information and job information. The work list includes the patient information and job information. The patient information may include the details of the patient for example name, address, age, sex, past medical records etc. The job information may include the details of the treatment like schedule of scanning, body part to be scanned, suitable imaging device needs to be used for scanning, concerned doctor, any other priority details etc. In an embodiment the database may have a route map of the hospital based on the hospital data, which may be fetched by the robotic controller while operation. The database may also have a navigation route stored, which may be fetched by the robotic control. The navigation route defines the movement paths of the imaging device 420.

The processor 430 in the robotic controller 425 is configured for generating signals for controlling the movement of the imaging device 420. The processor 430 receives instructions from the user interface 410 and accordingly generates signals, which can control the movements of the imaging device 420. The processor 430 will fetch hospital information including hospital layout plans, number of floors, scanning rooms, reference points, elevator details etc from the server 480. The server 480 is provided in the hospital which may have a database having hospital data including hospital layout plans, number of floors, scanning rooms, reference points, elevator details etc. Based on the hospital information the processor 430 generates a route map. The processor 430 also fetches a work list from the server 480. The server 480 may have a work list indicting patient information and job information. The patient information includes name, address, medical history, age sex, details of diagnostics to be done etc. The job information includes scanning schedule, desired imaging device, availability of the doctor, priority details etc. Again based on the route map and the work list the processor 430 will generate a navigation map.

In an embodiment the processor 430 is provided with a memory 435. The memory 435 may be used to store the hospital information, work list etc. The processor 430 may fetch the work list from the server 480 in a predefined interval and may store the same in the memory. Also the memory 435 in the processor 430 may be stored with previous scanning or medical reports of the patients scheduled for scanning and may be used by the doctor while scanning the patient. The past medical history may be available in the server 480 and may be fetched by the processor 430 upon request of the doctor or based on need.

In an embodiment the operator may send some emergency or alert signal based on situation. The processor 430 is configured to assign priority to the emergency situation and change the navigation route accordingly. Also the processor 430 is configured to ensure necessary security to the imaging device against unauthorized and wrong movements of the imaging device.

In an embodiment there are video, audio, control and status channels provided between the hospital environment 400 and the operator environment 450. The status channel may be provided for checking/updating the operating status of the imaging device 420. The control channel may be used to provide some control signals like emergency operations, priority details, initial authorization for operating the imaging device etc. The audio and video channels are used to communicate the aural and visual data form the user interface such as speaker, microphone, camera etc. The processor 430 may have CODEC circuits to convert the different forms of signals from different user interfaces to appropriate signals.

The processor 430 is operably coupled to moving assembly 440. The moving assembly 440 is associated with the housing of the robotic controller 425. The moving assembly 440 includes a moving mechanism to move the imaging device 420 in multi-direction. The moving assembly 440 is configured to receive signals from the processor 430 and move the imaging device 420 in accordance with the signals. In an embodiment the moving assembly 440 is a set of wheels, which are capable to drive the imaging device 420 in various directions.

In an embodiment the imaging device 420 may be fully automatically guided in a hospital environment. The processor 430 in the robotic controller 425 may fetch the work list from the server 480 in a predefined interval and this information may be stored in the memory 435. The processor 430 determines the navigation route based on the work schedule, which may be obtained from the work list and initialize the movement of the imaging device 420. This is achieved by sending some initialization signals to the moving assembly 430. The moving assembly 440 receives the signals and as per the instructions received from the processor 430 the moving assembly 440 will drive the imaging device 420 within the hospital. Thus the embodiment avoid the human intervention in moving the imaging device 420 is a hospital environment 400, providing a fully automated self-guided potable medical imaging system. Thus will it avoid the need of the operator environment 450.

The application of the invention need not be limited to the above mentioned examples. Various features and functions may be achieved by using different types of robotic controllers available in the industry. For example the robotic controller may send the scan report to different doctors for suggestion and may perform the scanning again, without actually going to the doctor for consulting. This will avoid the wastage of time.

Figure 5:
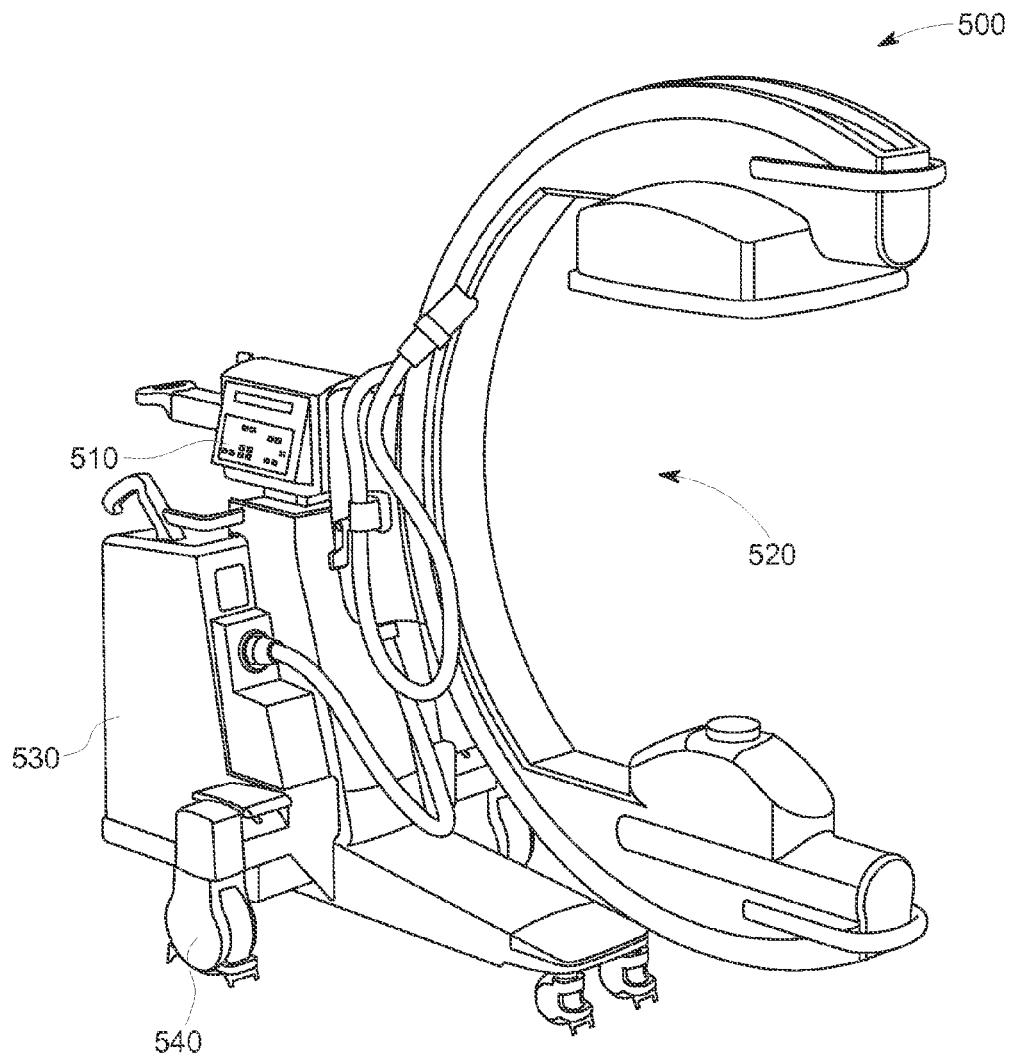
FIG. 5 is a schematic diagram of an imaging device using C-arm with an automatic moving mechanism as described in an embodiment of the invention.

FIG. 5 is a schematic diagram of an imaging system using C-Arm with an automatic moving mechanism as described in an embodiment of the invention. The C-Arm imaging system 500 is provided with a C-Arm imaging device 520. The imaging device 520 is provided with a user interface 510, which is configured to act as interface between an operator or user and the imaging device 520. A motion controller 530 is provided to generate signals or navigation route for controlling the movement of the imaging device 520. The motion controller 530 is coupled to a moving assembly 540. The moving assembly 540 is provided in association with the imaging device 520 and is configured to move the imaging device 520 in various directions. The moving assembly 540 receives signals from the motion controller 530 and moves the imaging device 520 in accordance with the signals. The functional aspects of the imaging system is same as that described in reference to FIG. 3.

Figure 6:
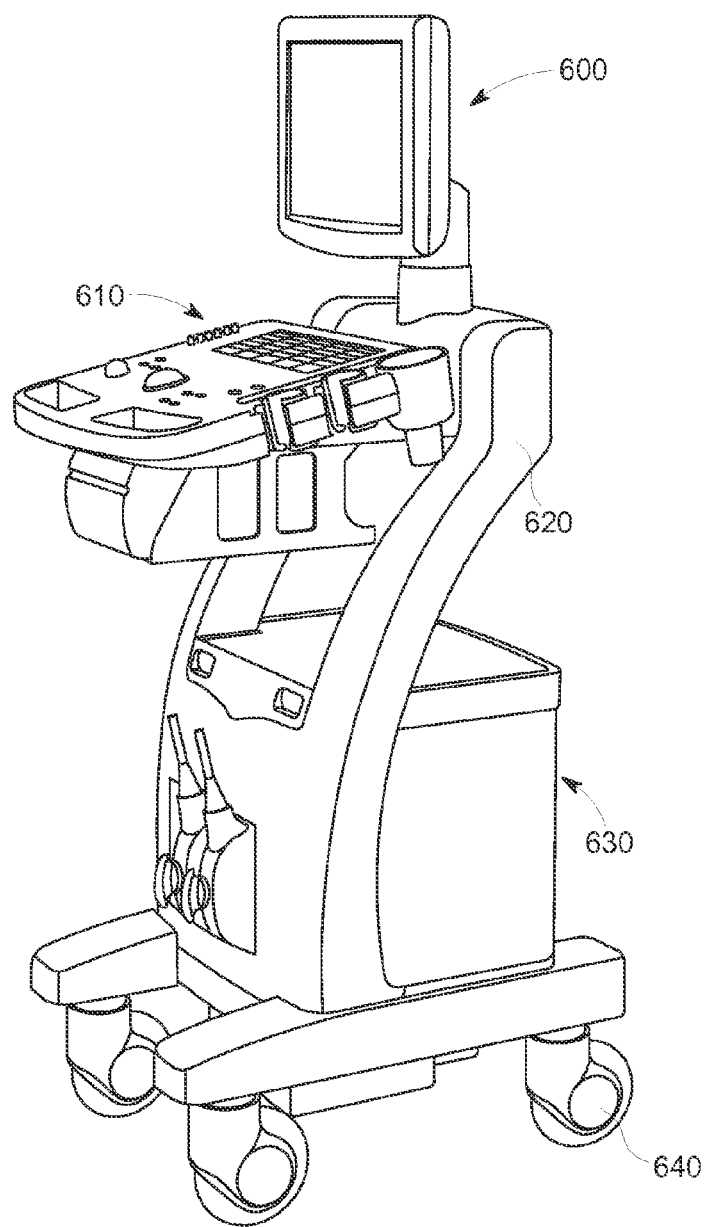
FIG. 6 is a schematic diagram of an ultrasound imaging device with an automatic moving mechanism as described in an embodiment of the invention.

FIG. 6 is a schematic diagram of an ultrasound imaging device with an automatic moving mechanism as described in an embodiment of the invention. The Ultrasound imaging system 600 is provided with an ultrasound imaging device 620. The imaging device 620 is provided with a user interface 610, which is configured to act as an interface between an operator or user with the imaging device 620. A motion controller 630 is provided to generate signals or navigation route for controlling the movement of the imaging device 620. The motion controller 630 is coupled to a moving assembly 640. The moving assembly 640 is provided in association with the imaging device 620 and is configured to move the imaging device 620 in various directions. The moving assembly 640 receives signals from the motion controller 630 and moves the imaging device 620 in accordance with the signals. The functional aspects of the imaging system 600 is same as that described in reference to FIG. 3.

Some of the advantages of the invention include reducing the efforts in physically moving the imaging system around hospital—which may be across multiple floors and multiple sections of the hospital, optimizing the scan session time and effort by integrating the location information of patients, visually representing the navigation route of the imaging system and helps the operator to use it for driving the imaging system through hospital. Also it enables integrations with a "robotic controller", to help the imaging system to drive itself to target locations with very little input from user.

Thus various embodiments of the invention describe a portable imaging device with an automatic moving mechanism and its methods. Further embodiments of the invention provide a self guided portable medical imaging system.

It should be noted that although the flow charts provided herein show a specific order of method steps, it is understood that the order of these steps may differ from what is depicted. Also, two or more steps may be performed concurrently or with partial concurrence. It is understood that such variations are within the scope of the invention.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

What is claimed is:

1. A medical diagnostic device with an automatic moving mechanism, comprising:
    an input interface for receiving instructions;
    a motion controller coupled to the input interface for controlling movements of the medical diagnostic device based on a work list, the work list including patient information and job information, the job information including at least one of schedule of scanning, body part to be scanned, suitable imaging device needs to be used for scanning, or availability of doctor, wherein the motion controller is configured to automatically control movements of the medical diagnostic device based on the work list without manual control by a user; and
    a moving assembly coupled to the motion controller for automatically moving the medical diagnostic device under control of the motion controller, the movement being controlled in accordance with a navigation route automatically generated by the motion controller based on the work list.

2. A medical diagnostic device as in claim 1, wherein the input interface is a user interface, and the instructions represent movements commanded by a user.

3. A medical diagnostic device as in claim 2, wherein the moving assembly is configured to receive signals from the motion controller for moving the medical diagnostic device under manual control of the user.

4. A medical diagnostic device as in claim 1, wherein the input interface is configured to receive the instructions from a remote device.

5. A medical diagnostic device as in claim 1, wherein the medical diagnostic device is a medical imaging device.

6. A medical diagnostic device as in claim 5, wherein the medical imaging device is selected from a group consisting of a computed tomography imaging device, a positron emission tomography imaging device, a magnetic resonance imaging device, an ultrasound imaging device and an X-ray imaging device.

7. A medical diagnostic device as in claim 1, wherein the medical diagnostic device is a patient monitoring device.

8. A medical diagnostic device as in claim 7, wherein the patient monitoring device is selected from a group consisting of an electrocardiographic monitoring device, a blood pressure monitoring device, and an anesthesia monitoring device.

9. A medical diagnostic device as in claim 1, wherein the input interface is a wireless interface.

10. A medical diagnostic device as in claim 1, wherein the motion controller is configured to receive the instructions from the input interface and to generate control signals based on the instructions, the control signals applied to the moving assembly for controlling movements of the medical diagnostic device.

11. A medical diagnostic device as in claim 1, wherein the moving assembly is configured to allow a linear and a 360 degree rotational movement of the medical diagnostic device.

12. The medical diagnostic device as in claim 1, wherein the motion controller is configured to automatically change the navigation route while on the navigation route based on a received input, and wherein the change in the navigation route alters an order of patients to be visited along the navigation route in response to the received input.

13. The medical diagnostic device as in claim 1, wherein the job information includes the availability of the doctor.

14. The medical diagnostic device as in claim 1, wherein the job information includes the suitable imaging device needs to be used for scanning.

15. The medical diagnostic device as in claim 1, wherein the job information includes the schedule of scanning, the body part to be scanned, the suitable imaging device needs to be used for scanning, and the availability of the doctor.

16. A self-guided portable medical imaging system comprising:
    a medical imaging device;
    a robotic controller coupled to the medical imaging device, the robotic controller comprising: a processor configured to automatically guide the movement of the medical imaging device using a work list and a route map, the work list including patient information and job information, the job information including at least one of schedule of scanning, body part to be scanned, suitable imaging device needs to be used for scanning, or availability of doctor; and a moving assembly operably coupled to the processor for automatically moving the medical imaging device in accordance with a navigation route automatically generated by the robotic controller based on the work list.

17. A self-guided portable medical imaging system as in claim 16, wherein the processor is configured to fetch the work list automatically from a server on a predefined interval.

18. A self-guided portable medical imaging system as in claim 17, wherein the processor is further configured to automatically generate the route map from hospital data, the hospital data being fetched from the server.

19. A self-guided portable medical imaging system as in claim 18, wherein the processor is further configured to automatically generate the navigation route using the route map for controlling the moving assembly.

20. A self-guided portable medical imaging system as in claim 19, wherein the processor is further configured to provide security to the imaging device from unauthorized usage.

21. A self-guided portable medical imaging system as in claim 16, wherein the robotic controller comprises a user interface configured to receive movement commands from a user to manually direct the movement of the medical imaging device.

22. A self-guided portable medical imaging system as in claim 16, wherein the imaging device is one of a computed tomography device, a positron emission tomography device, a magnetic resonance imaging device, an ultrasound imaging device and an X-ray device.

* * * * *